(12) United States Patent
Meyer et al.

(10) Patent No.: US 9,089,625 B2
(45) Date of Patent: Jul. 28, 2015

(54) BONE CEMENT COMPOSITION AND METHOD OF MAKING THE SAME

(75) Inventors: Jörg Meyer, Heusenstamm (DE); Robert Wenz, Wöllstadt (DE)

(73) Assignee: KYPHON SARL, Neuchatel (CH)

( * ) Notice: Subject to any disclaimer, the term of this patent is extended or adjusted under 35 U.S.C. 154(b) by 648 days.

(21) Appl. No.: 12/635,095

(22) Filed: Dec. 10, 2009

(65) Prior Publication Data

US 2010/0086620 A1   Apr. 8, 2010

Related U.S. Application Data

(62) Division of application No. 11/214,151, filed on Aug. 29, 2005, now Pat. No. 7,651,701.

(51) Int. Cl.
*A61K 9/14* (2006.01)
*A61L 24/00* (2006.01)
*A61K 31/66* (2006.01)
*A61K 38/18* (2006.01)
*A61L 24/04* (2006.01)

(52) U.S. Cl.
CPC ............. *A61L 24/0084* (2013.01); *A61K 31/66* (2013.01); *A61K 38/18* (2013.01); *A61L 24/04* (2013.01)

(58) Field of Classification Search
CPC .... A61K 31/66; A61K 38/18; A61L 24/0084; A61L 24/04; A61L 24/06; A61L 24/043
See application file for complete search history.

(56) References Cited

U.S. PATENT DOCUMENTS

| | | |
|---|---|---|
| 4,141,864 A | 2/1979 | Rijke et al. |
| 4,192,021 A | 3/1980 | Deibig et al. |
| 4,239,113 A | 12/1980 | Gross et al. |
| 4,341,691 A | 7/1982 | Anuta |
| 4,404,327 A | 9/1983 | Crugola et al. |
| 4,518,430 A | 5/1985 | Brown et al. |
| 4,588,583 A | 5/1986 | Pietsch et al. |
| 4,612,053 A | 9/1986 | Brown et al. |
| 4,629,464 A | 12/1986 | Takata et al. |
| 4,678,436 A | 7/1987 | Kondo et al. |
| 4,722,948 A | 2/1988 | Sanderson |
| 4,791,150 A | 12/1988 | Braden et al. |
| 4,872,936 A | 10/1989 | Engelbrecht |
| 4,902,649 A | 2/1990 | Kimura et al. |
| 4,940,689 A | 7/1990 | Ito |
| 4,957,352 A | 9/1990 | Yasuda et al. |
| 4,959,104 A | 9/1990 | Iino et al. |
| 5,004,501 A * | 4/1991 | Faccioli et al. ................. 106/35 |
| 5,108,956 A | 4/1992 | Inoue et al. |
| 5,149,368 A | 9/1992 | Liu et al. |
| 5,160,371 A | 11/1992 | Ito |
| 5,171,720 A | 12/1992 | Kawakami |
| 5,179,065 A | 1/1993 | Ito |
| 5,205,928 A | 4/1993 | Inoue et al. |
| 5,262,166 A | 11/1993 | Liu et al. |
| 5,276,070 A | 1/1994 | Arroyo |
| 5,281,265 A | 1/1994 | Liu |
| 5,352,715 A | 10/1994 | Wallace et al. |
| 5,462,356 A | 10/1995 | Murray |
| 5,522,893 A | 6/1996 | Chow et al. |
| 5,545,254 A | 8/1996 | Chow et al. |
| 5,605,713 A | 2/1997 | Boltong |
| 5,650,108 A | 7/1997 | Nies et al. |
| 5,695,729 A | 12/1997 | Chow et al. |
| 5,702,677 A | 12/1997 | Shimp et al. |
| 5,795,922 A * | 8/1998 | Demian et al. ................. 523/117 |
| 5,797,873 A | 8/1998 | Franz et al. |
| 5,814,683 A | 9/1998 | Branham |
| 5,847,046 A | 12/1998 | Jiang et al. |
| 5,914,356 A | 6/1999 | Erbe |
| 5,952,010 A | 9/1999 | Constantz |
| 6,075,067 A | 6/2000 | Lidgren |
| 6,124,373 A | 9/2000 | Peter et al. |
| 6,153,664 A | 11/2000 | Wise et al. |
| 6,187,046 B1 | 2/2001 | Yamamoto et al. |
| 6,203,574 B1 | 3/2001 | Kawamura |
| 6,206,957 B1 | 3/2001 | Driessens et al. |
| 6,231,615 B1 | 5/2001 | Preissman |

(Continued)

FOREIGN PATENT DOCUMENTS

| | | |
|---|---|---|
| DE | 29607832 | 10/1996 |
| DE | 20218668 | 3/2003 |

(Continued)

OTHER PUBLICATIONS

Henning T. polyethylene glycols (PEGs) and the pharmaceutical industry, Fine, Specialty & Performance Chemicals (PHARMACHEM), Jun. 2002, pp. 57-59.*

Abdullah et al., Biodegradable Polymeric Bone Cement Formed from Hydroxyapatite, Poly (Propylene Fumerate), Poly (Vinyl Pyrrolidone) and Benzoyl Peroxide, Materials Science and Technology, vol. 20, No. 9, pp. 1084-1086 (2004) (abstract only).

Baroud et al., Influence of Oscillatory Mixing on the Injectability of Three Acrylic and Two Calcium-Phosphate Bone Cements for Vertebroplasty, J Biomed Mater Res, vol. 68B, No. 1, pp. 105-111 (2004) (abstract only).

(Continued)

*Primary Examiner* — Satyendra Singh
(74) *Attorney, Agent, or Firm* — Sorell Lenna & Schmidt LLP

(57) ABSTRACT

Disclosed herein is a composition suitable for use in spinal surgery. The composition generally includes a reaction product or settable mixture of first and second components, the first component including a spray-dried inorganic filler, a radical donor, and a pre-polymerized vinyl polymer, and the second component including a radical scavenger, a diluent, a polymerization accelerator, and a reactive monomer. Furthermore, disclosed herein is a method of making the composition, which generally includes mixing the first and second components under conditions suitable to form a curable reaction product.

20 Claims, No Drawings

(56) References Cited

U.S. PATENT DOCUMENTS

| | | | |
|---|---|---|---|
| 6,241,734 | B1 | 6/2001 | Scribner et al. |
| 6,273,916 | B1 | 8/2001 | Murphy |
| 6,309,420 | B1 | 10/2001 | Preissman |
| 6,325,992 | B1 | 12/2001 | Chow et al. |
| 6,497,901 | B1 | 12/2002 | Royer |
| 6,521,264 | B1 | 2/2003 | Lacout et al. |
| 6,547,866 | B1 | 4/2003 | Edwards et al. |
| 6,562,755 | B1 | 5/2003 | Halbrook, Jr. et al. |
| 6,593,394 | B1 | 7/2003 | Li et al. |
| 6,613,054 | B2 | 9/2003 | Scribner et al. |
| 6,692,563 | B2 | 2/2004 | Zimmermann |
| 6,908,506 | B2 | 6/2005 | Zimmermann |
| 6,953,594 | B2 | 10/2005 | Lee et al. |
| 6,994,726 | B2 | 2/2006 | Lin et al. |
| 7,008,433 | B2 | 3/2006 | Voellmicke et al. |
| 7,115,163 | B2 | 10/2006 | Zimmermann |
| 7,138,442 | B2 | 11/2006 | Smith et al. |
| 7,160,932 | B2 | 1/2007 | Schilke et al. |
| 7,273,523 | B2 | 9/2007 | Wenz |
| 2001/0012968 | A1 | 8/2001 | Preissman |
| 2002/0152929 | A1 | 10/2002 | Burgath et al. |
| 2002/0167480 | A1 | 11/2002 | Johnson et al. |
| 2002/0187104 | A1 | 12/2002 | Li et al. |
| 2002/0191487 | A1 | 12/2002 | Sand |
| 2003/0031698 | A1 | 2/2003 | Roeder et al. |
| 2003/0032964 | A1 | 2/2003 | Watkins et al. |
| 2003/0055512 | A1 | 3/2003 | Genin et al. |
| 2003/0139488 | A1 | 7/2003 | Wojciak |
| 2003/0161858 | A1 | 8/2003 | Lidgren |
| 2003/0180344 | A1 | 9/2003 | Wise et al. |
| 2004/0048947 | A1 | 3/2004 | Lidgren et al. |
| 2004/0122359 | A1 | 6/2004 | Wenz et al. |
| 2004/0157952 | A1 | 8/2004 | Soffiati et al. |
| 2004/0226479 | A1 | 11/2004 | Lyles et al. |
| 2004/0265385 | A1 | 12/2004 | West |
| 2005/0105384 | A1 | 5/2005 | Eder et al. |
| 2005/0142211 | A1 | 6/2005 | Wenz |
| 2005/0199156 | A1 | 9/2005 | Khairoun et al. |
| 2005/0246036 | A1 | 11/2005 | Zimmermann |
| 2005/0256220 | A1 | 11/2005 | Lavergne et al. |
| 2006/0079905 | A1 | 4/2006 | Beyar et al. |
| 2007/0021526 | A1 | 1/2007 | He et al. |
| 2007/0032567 | A1 | 2/2007 | Beyar et al. |
| 2007/0048382 | A1 | 3/2007 | Meyer et al. |
| 2007/0128245 | A1 | 6/2007 | Rosenberg et al. |
| 2007/0191964 | A1 | 8/2007 | Preissman |
| 2007/0254011 | A1 | 11/2007 | Schnabelrauch et al. |

FOREIGN PATENT DOCUMENTS

| | | |
|---|---|---|
| DE | 20218668 U1 | 3/2003 |
| EP | 0473048 A2 | 3/1992 |
| EP | 0511868 A2 | 11/1992 |
| EP | 0520690 A2 | 12/1992 |
| EP | 0543765 A1 | 5/1993 |
| EP | 1002513 A1 | 5/2000 |
| EP | 1255576 B1 | 8/2003 |
| EP | 0835668 B1 | 11/2007 |
| JP | 01320251 | 12/1989 |
| JP | 02116684 | 5/1990 |
| WO | WO9202478 A1 | 2/1992 |
| WO | WO9513835 A1 | 5/1995 |
| WO | WO9614265 A1 | 5/1996 |
| WO | WO0149327 A2 | 7/2001 |
| WO | WO0232827 A1 | 4/2002 |
| WO | WO0236518 A1 | 5/2002 |
| WO | WO03086327 A2 | 10/2003 |
| WO | WO03103734 A1 | 12/2003 |
| WO | WO2004050131 A1 | 6/2004 |
| WO | WO2005009481 A2 | 2/2005 |
| WO | WO2007025633 A2 | 3/2007 |
| WO | WO2007067561 A2 | 6/2007 |

OTHER PUBLICATIONS

Beruto et al., Use of Alpha-Tricalcium Phosphate (TCP) as Powders and as an Aqueous Dispersion to Modify Processing, Microstructure, and Mechanical Properties of Polymethylmethacrylate (PMMA) Bone Cements and to Produce Bone-Substitute Compounds, J Biomed Mater Res, vol. 49, No. 4, pp. 498-505 (2000) (abstract only).

Bezzi G. et al., A novel sol-gel technique for hydroxyapatite preparation, Materials Chemistry and Physics, 2003, 78: 816-824, entire document.

Bonfield et al., Hydroxyapatite Composite Biomaterials—Evolution and Applications, Materials World, vol. 5, No. 1, pp. 18-20 (1997).

Brown, et al., A new calcium phosphate, water-setting cement, Cements Research Progress 1986 pp. 352-379 (1987).

Canul-Chuil et al., Comparative Study of Bone Cements prepared with either HA or alpha-TCP and Functionalized Methacrylates, J Biomed Mater Res, vol. 64B. No. 1, pp. 27-37 (2003) (abstract only).

Chu et al., Hydroxyapatite/PMMA Composites as Bone Cements, Biomed Mater Eng, vol. 14, No. 1, pp. 87-105 (2004) (abstract only).

Dalby et al., Initial Interaction of Osteoblasts with the Surface of a Hydroxyapatite-Poly (Methylmethacrylate) Cement, Biomaterials, vol. 22, No. 13, pp. 1739-1747 (2001) (abstract only).

Eule et al., Bioactive Bone Cement: The Solution for Osteolysis and Late Implant Loosening, SRS Annual Meeting: Scientific Program Abstracts, pp. 98 (2002).

Frankenburg et al., Evaluation of Hydroxyapatite/Bis-GMA Bone Cement for Fixation of Cemented Hip Stems, The Third Combined Meeting of the Orthopaedic Research Societies of the USA, Canada, Europe and Japan, Hamamatsu City, Japan (1998).

Grigorian et al., Evolution of Tissue Structures in the Mandible after Implantation of Plate from Polymethylmethacrylate and its Compositions with Hydroxyapatite, Stomatolgiia, vol. 82, No. 2, pp. 10-14 (2003) (abstract only).

Harper et al., Tensile Characteristics of Ten Commerical Acrylic Bone Cements, J Biomed Mater Res:Appl Biomater., vol. 53, pp. 605-616 (2000) (abstract only).

Heness et al., Biocomposites—Bone Cement, Hydroxyapatite and Biomimetic Composites for Bone Repair, Innovative Bioceramics, Materials Forum, vol. 27 (2004) (3 page abstract).

Hitchon et al., Comparison of the Biomechanics of Hydroxyapatite and Polymethylmethacrylate Vertebroplasty in a Cadaveric Spinal Compression Fracture Model, J. Neurosurg, vol. 95, Suppl. 2, pp. 215-220, (2001) (abstract only).

Ishikawa et al,, Effects of neutral sodium hydrogen phosphate on setting reaction and mechanical strength of hydroxyapatite putty, J Biomed Mater Res, 44, 322-329, 1999.

Ishikawa et al., Non-decay type fast-setting calcium phosphate cement Hydroxyapatite putty containing an increased amount of sodium alginate, J Biomed Mater Res, 36, 393-399, 1997.

Jager et al., Comprehensive Biocompatibility Testing of a New PMMA-hA Bone Cement Versus Conventional PMMA Cement in Vitro, J. Biomater Sci Polym Ed, vol. 14, No. 11, pp. 1283-1298 (2003) (abstract only).

Lee C L et al., Laser Ablation of Dyed Acrylic Bone Cement, Lasers in Surgery and Medicine, Wiley-Liss, New York, US vol. 20, 3, Jan. 1, 1997, pp. 280-289, XP000694435, ISSN:0196-8092.

Lee R.R. et al, Interactions between bone and hydroxyapatite filled 4 META/MMA-TBB adhesive cement in vitro and in physiological environment, 1996, IEEE Xplore, pp. 18-21, entire document.

Li et al., A Novel Injectable Bioactive Bone Cement for Spinal Surgery: A Developmental and Preclinical Study, J Biomed Mater Res, vol. 52, No. 1,,pp. 164-170 (2000) (abstract only).

Liu et al., Influence of the Aspect Ratio of Bioactive Nanofillers on Rheological Behavior of PMMA-Based Orthopedic Materials, J Biomed Mater Res, vol. 71B, No. 1, pp. 116-122 (2004) (abstract only).

Liao et al., A Fundamental Study on Bioreactions of Sr-HA, Hua Xi Kou Qiang Yi Xue Za Zhi, vol. 20, No. 3, pp. 172-174 183 (2002) (abstract only).

Miyazaki et al., Bioactive PMMA Bone Cement Prepared by Modification with Methacryloxypropyltrimethoxysilane and Calcium Chloride, J Biomed Mater Res, vol. 67A, No. 4, pp. 1417-1423 (2003) (abstract only).

(56) References Cited

OTHER PUBLICATIONS

Mousa et al., Biological and Mechanical Properties of PMMA-Based Bioactive Bone Cements, Biomaterials, vol. 21, No. 21, pp. 2137-2146 (2000) (abstract only).
Okada et al., Transmission Electron Microscopic Study of Interface Between Bioactive Bone Cement and Bone: Comparison of Apatite and Wollastonite Containing Glass-Ceramic Filler with Hydroxyapatite and Beta-Tricalcium Phosphate Filler, J Biomed Mater Res, vol. 45, No. 4, pp. 277-284 (1999) (abstract only).
Oonishi et al., Hydroxyapatite Granules Interposed at Bone-Cement Interface in Total Hip Replacements: Histological Study of Retrieved Specimens, J Biomed Mater Res, vol. 53, No. 2, pp. 174-180 (2000) (abstract only).
Patel et al., Comparison of Sintering and Mechanical Properties of Hydroxyapatite and Silicon-Substituted Hydroxyapatite, Key Engineering Materials, 240-242, 919-22 (2003) (abstract only).
Patent Abstract XP-002180738 (1 page total), Park et al., "Compositional effects of CaO-SiO2-P2O5 bioactive cement on hardening and hydroxyapatite formation" Yoop Hakhoechi, 31(5):502-512 (1994).
Patent Abstract XP-002180739 (1 page total), Nippon Electric Glass Co., "Bone-repair material for fast, strong bonding—contains glass and/or crystalline glass powder, a.q. phosphate solution and bond formation promoter" (1992).
The term "PRE-", Merriam-Webster Online Dictionary, at the web: http://www.m-w.com, p. 1-2, Accessed on Sep. 17, 2006.
Serbetci et al., Mechanical and Thermal Properties of Hydroxyapatite-Impregnated Bone Cement, Turk J Med Sci, vol. 30, pp. 543-549 (2000) (abstract only).
Turner et al., Hydroxyapatite Composite Resin Cement Augmentation of Pedicle Screw Fixation, Clinical Orthopaedics & Related Research, vol. 1, No. 406, pp. 253-261 (2003) (abstract only).
Wong et al., In Vivo Cancellous Bone Remodeling on a Strontium-Containing Hydroxyapatite (sr-HA) Bioactive Cement, J Biomed Mater Res A, vol. 68, No. 3, pp. 513-521 (2004) (abstract only).).
Wong et al., Ultrastructural Study of Mineralization of a Strontium-Containing Hydroxyapatite (Sr-HA) Cement in Vivo, J Biomed Mater Res A, vol. 70, No. 3, pp. 428-435 (2004) (abstract only.
Zhao et al., Surface Treatment of Injectable Strontium-Containing Bioactive Bone Cement for Vertebroplasty, J. Biomed Mater Res B Appl Biomater, vol. 69, No. 1, pp. 79-86 (2004) (abstract only).
International Search Report, WIPO, Jan. 22, 2009.
International Search Report and Written Opinion, International Application No. PCT/US2007/012723, mailed Dec. 3, 2008.
International Search Report and Written Opinion, International Application No. PCT/US2007/008789, mailed Nov. 13, 2008.
International Search Report and Written Opinion, International Application No. PCT/EP2006/007750, mailed Jun. 11, 2007.
International Search Report, International Application No. PCT/US03/38580, mailed May 19, 2004.
International Search Report, International Application No. PCT/US2005/014616, mailed Sep. 12, 2005.
Heini, P.F., et al., "Bone substitutes in vertebroplasty," *Eur. Spine J.*, Jun. 14, 2001, vol. 10, pp. S205-S213.
Li, Y., et al. "Preparation of amorphous calcium phosphate in the presence of poly(ethylene glycol)," *Journal of Materials Science Letters*, 2003, vol. 22, pp. 1015-1016.

\* cited by examiner

BONE CEMENT COMPOSITION AND METHOD OF MAKING THE SAME

Division of application Ser. No. 11/214,151, filed on Aug. 29, 2005, now U.S. Pat. No. 7,651,701.

BACKGROUND OF THE DISCLOSURE

1. Field of the Disclosure

The disclosure generally relates to compositions useful as bone cements and, more specifically, to compositions useful in spinal surgery, a kit containing packaged components of the composition, and a method of making the composition.

2. Brief Description of Related Technology

Bone cement compositions are known to be useful in bonding or affixing an implant material to natural bone and to otherwise repair damaged natural bone. These compositions are especially useful in orthopedic and dental procedures. Although bone cement compositions enjoy wide use in the medicinal arts, these compositions need to be carefully designed depending on the surgical site at which they will be used. For example, compositions suitable for use in repairing a damaged bone in a limb may not be ideally suited for use in repairing damaged teeth. Similarly, compositions useful in repairing a limb or a tooth may not be ideally suited for surgically repairing the spinal column.

Spinal surgery is complex and risky given the proximity of the surgical site to the spinal cord and major organs. Conventional spinal surgery can repair fractured vertebrae and restore a patient's height, but it is highly invasive and involves significant risks. These surgeries involve making long incisions in the patient's chest or back so that metal instruments can move the fractured bones back into their normal positions. However, the instruments used in these surgeries are not optimally designed to manipulate deteriorated bone. The bones are then held in place by metal implants, which in the case of elderly patients with osteoporosis, can fail to hold due to the softness of the inner cancellous bone to which the implants are affixed or bonded. Consequently, conventional spinal surgery is performed in rare circumstances. Even when it is performed, the invasiveness of the procedure can result in damage to the spinal cord, pain, infection, and other disorders requiring post-operative, corrective procedures.

Recent developments in spinal surgery have made it possible to reduce the invasiveness prevalent in conventional procedures, thereby reducing some of the risks historically associated with the procedures. Among those developments are developments in compositions used to bond implants to natural bone or act as bone substitutes themselves. Another recent development is the ability to use syringe-like devices to deliver these compositions to the surgical site in a non-invasive manner. Suitable devices and delivery methods are disclosed in U.S. Pat. Nos. 6,241,734 and 6,613,054, and U.S. patent application Publication Nos. 2004/0122359 and 2002/0191487, the disclosures of which are incorporated herein by reference. In combination, conventional bone cement compositions along with the improved delivery methods these publications describe can reduce the invasiveness of conventional spinal surgery making the procedure a more viable option for patients in need of treatment.

Typically, current bone cement compositions are sold in two-part preparations containing a powder (or dry) part and a liquid (or wet) part, which, when combined, polymerize to form a hardened substance mimicking many of the physical properties of natural bone. The powder part includes a filler and a polymeric material, while the liquid part includes a reactive monomer (e.g., methylmethacrylate). The filler is a material that is bioactive on its surface to promote the natural growth of bone thereon. An example of such a filler is hydroxyapatite. Hydroxyapatite has a large surface area that undesirably absorbs the reactive monomer. Thus, the current preparations contain an excess amount of reactive monomer because a portion of the reactive monomer is absorbed into the hydroxyapatite and, therefore, does not participate in the polymerization reaction. When the two parts are combined to form the preparation and applied in practice, the monomer can undergo an exothermic reaction as the composition hardens. This heat generated by the reaction is highly undesirable because it can damage nerves, bones, and surrounding tissue, for example. This is especially undesirable in spinal surgery due to the proximity of the spinal cord. Additionally, the presence of the reactive monomer can result in undesired shrinkage of the composition after polymerization—diminishing bond quality between the composition and the bone to which the composition is bonded/applied. Moreover, the reactive monomer can be toxic to a patient if present in large amounts. Thus, the less the amount of reactive monomer necessary in the composition the less likely that the composition will experience undesired shrinkage, and the reduced incidences of patient exposure to heat and toxic materials.

Accordingly, there is a need for an improved bone cement composition including a reduced amount of reactive monomer, and a filler with a suitable surface area, particle size, and rheological properties for the intended use of the composition.

DETAILED DESCRIPTION OF THE PREFERRED EMBODIMENTS

Disclosed herein is a composition comprising a reaction product or a settable mixture of first and second components, the first component including a spray-dried inorganic filler, a radical donor, and a pre-polymerized vinyl polymer, and the second component including a radical scavenger, a diluent, a polymerization accelerator, and a reactive monomer. Also disclosed herein is a method of making the composition, which generally includes mixing the first and second components under conditions suitable to form the reaction product. The first component also can be referred to as a the dry or powder component as that is its usual physical state. Similarly, the second component also can be referred to as a wet or liquid component as that is its usual physical state. Also disclosed herein is a kit where the first and second components are maintained apart from each other (e.g., separately packaged or contained) until they are ready for use in forming the composition.

As described hereinafter, embodiments of the combination of ingredients comprising the first and second components advantageously provides a bone cement composition that overcomes deficiencies heretofore unaddressed in the field. Specifically, the first component includes a spray-dried inorganic filler. Suitable inorganic fillers include tricalcium phosphate, tetracalcium phosphate, hydroxyapatite, fluoride-substituted hydroxyapatite, strontium-substituted hydroxyapatite such as those disclosed in international publication WO 03/103734, the disclosure of which is incorporated herein by reference.

In one embodiment, the inorganic filler is spray-dried and can be prepared by mixing a commercially-available inorganic filler with an organic solvent to obtain a mixture that is then spray-dried using conventional spray-drying mechanisms and techniques to provide the spray-dried inorganic filler. Preferably, the spray-dried inorganic filler is a spray-dried hydroxyapatite and is prepared by mixing a commercially-available hydroxyapatite with an organic solvent to obtain a mixture, which is then spray-dried using conventional spray-drying mechanisms and techniques, resulting (with additional sintering) in a 60-fold reduction in surface area. Hydroxyapatite is commercially available from a variety of sources, such as, for example, Merck KGaA (Germany). Precipitated inorganic fillers, such as precipitated hydroxyapatite also can be spray-dried and used in the composition and in accordance with the disclosed method of making the composition.

The organic solvent can be any organic liquid that can be readily volatilized when spray-dried using conventional spray-drying mechanisms and techniques. Preferably, however, the organic solvent is selected from the group consisting of polyvinyl alcohol (PVA), polyvinyl pyrrolidine (PVP), acetone, alcohols, polyethylene glycol (PEG), oils of fatty acids, and mixtures thereof. Among the organic solvents, PVA is more highly preferred.

Next, the spray-dried inorganic filler should be sintered at a temperature of about 900° C. to about 1280° C. for about ten minutes per kilogram to about five hours per kilogram, preferably at a temperature of about 1200° C. to about 1240° C. for about 30 minutes per kilogram to about two hours per kilogram. The resultant, sintered and spray-dried inorganic filler can than be easily broken into smaller pieces to obtain a sintered, spray-dried inorganic filler having a preferred particle size falling within the range of particle size for the pre-polymerized vinyl polymer (i.e., about 20 micrometers (μm) to about 55 μm), described below. Additionally, because the components of the composition and the composition itself will likely have to traverse a narrow and possibly tortuous path through a syringe-like devices and/or other delivery mechanisms to the surgical site, it is desirable to utilize materials that will not clog the path. Consequently, the smaller the particle size, the less likely the material will clog this path.

The first component generally includes about 0.5 wt. % to about 99.5 wt. % of the spray-dried inorganic filler, based on the total weight of the first component. Preferably, the first component includes about 10 wt. % to about 70 wt. % of the filler, and even more preferably about 30 wt. % to about 50 wt. % of the filler, based on the total weight of the first component.

As noted above, the first component can also include a pre-polymerized vinyl polymer. Preferably, the pre-polymerized vinyl polymer is selected from the group consisting of poly(methyl methacrylate) (PMMA), prepolymerized styrene acrylates, poly-methacrylate, poly-ethacrylate, poly-butylmethacrylate, and copolymers thereof, and mixtures thereof. As noted above, preferably the pre-polymerized vinyl polymer comprises beads having an average particle size of about 20 μm to about 35 μm. Preferably, the pre-polymerized vinyl polymer is PMMA.

The first component generally includes about 0.5 wt. % to about 99.5 wt. % of the pre-polymerized vinyl polymer, based on the total weight of the first component. Preferably, the first component includes about 50 wt. % to about 90 wt. % of the pre-polymerized vinyl polymer, and even more preferably about 30 wt. % to about 70 wt. % of the pre-polymerized vinyl polymer, based on the total weight of the first component.

A radical donor also is present in the first component. As described in more detail below, the radical donor is used to initiate a polymerization reaction with the reactive monomer present in the second component. Preferably, the radical donor is selected from the group consisting of benzoyl peroxide (BPO), azo-bis-isobutyrylnitrile (AIBN), and mixtures thereof.

In one embodiment, the balance of the first component generally is made up of the radical donor. Thus, the first component can include about 0.5 wt. % to about 5 wt. % of the radical donor, based on the total weight of the spray-dried inorganic filler and the pre-polymerized vinyl polymer. Preferably, the first component includes about 0.6 wt. % to about 3 wt. % of the radical donor, and even more preferably about 0.9 wt. % to about 2 wt. % of the radical donor, based on the total weight of the spray-dried inorganic filler and the pre-polymerized vinyl polymer.

Optionally, the first component can include an ingredient selected from the group consisting of antibiotics, cytostatic agents, analgesic agents, disinfectants, preservatives, growth factors, proliferative factors, proteins, peptides, biopolymers, imageable markers, dyes, and mixtures thereof. Particularly preferred ingredients among the foregoing include those selected from the group consisting of gentamycine, trombamycine, clindamycine, vancomycine, β-TGF or an analog thereof, a bone morphogenic protein series compound, and mixtures thereof.

Suitable imageable markers include, but are not limited to, barium sulfate ($BaSO_4$), zirconium dioxide, $CHI_3$, $Na_2FPO_3$, and $CaF_2$. Among these markers, barium sulfate is preferred. If present, the imageable marker may comprise up to 30 wt. % of the first component. To the extent an imageable marker is present, it will reduce the amount of spray-dried inorganic filler present in the first component. The imageable marker is not a necessary component. Instead, its presence in the composition would assist a user (e.g., a surgeon) in visualizing the application of the composition to a surgical site via an image-readable device (e.g., a fluoroscope in the case of barium sulfate). The presence of the imageable marker, therefore, does not impart any mechanical attributes to the composition—it is merely an aid to assist the user.

Similarly, a dye, if present does not impart any mechanical attributes to the composition—it also is merely an aid to assist the user (e.g., surgeon, medical technician, aid, or nurse). For example, the dye could be used to readily inform the surgeon of the type of composition he/she is using. A purple-colored dye may have become known in the field by users to be indicative of a bone cement composition suitable for use in the spine, whereas a different color material may be known in the art by users to be indicative of a bone cement composition suitable for another application.

As described above, in one embodiment, the second component can include a polymerization accelerator, a reactive monomer, a diluent, and a radical scavenger. Preferably, the polymerization accelerator is selected such that the polymerization reaction occurs at or below normal body temperatures so as not to cause damage to the surgical site and surrounding areas. The polymerization accelerator preferably is a tertiary amine. Suitable tertiary amines include, but are not limited to, dimethylparatoluidine (DMPT) and dihydroxyethylorthotoluidine. Although, DMPT is believed to be toxic to humans, in low concentrations, it may still be used without adverse consequences.

The second component generally includes about 0.1 wt. % to about 3 wt. % of the polymerization accelerator, based on the total weight of second component. Preferably, the second component includes about 0.2 wt. % to about 2 wt. % of the polymerization accelerator, and even more preferably about 0.3 wt. % to about 0.4 wt. % of the polymerization accelerator, based on the total weight of the second component.

A reactive monomer also is present in the second component. The reactive monomer is selected from the group consisting of methyl methacrylate (MMA), PEG monoacrylates, PEG diacrylates, PEG monomethacrylates, PEG dimethacrylates, PEG-mono/di-acrylate/methacrylate, butanediol methacrylates, polyolefin-acrylates, urethaneacrylates, methacrylates, and mixtures thereof. Among the PEG-based reactive monomers, those having a molecular weight in a range of about 200 Daltons (D) to about 1500 D are preferred. Preferably, the reactive monomer is MMA.

The second component generally include about 10 wt. % to about 99 wt. % of the reactive monomer, based on the total weight of the second component. Preferably, the second component includes about 40 wt. % to about 95 wt. % of the reactive monomer, and even more preferably about 60 wt. % to about 90 wt. % of the reactive monomer, based on the total weight of the second component.

In one embodiment, the second component can also include a diluent. Suitable diluents include, but are not limited to, polyethylene glycol (PEG), an ester of mellitic acid, and mixtures thereof. Preferably, the diluent is PEG. When present, a preferred ester of mellitic acid is tri-octylmellitic ester. Generally, the diluent should have a molecular weight such that the diluent remains in liquid form at room temperature. When PEG is used, preferably its molecular weight is about 100 D to about 1000 D, and more preferably about 400 D to about 800 D. The presence of the diluent in the second component provides multiple benefits. For example, the diluent desirably provides the ability to control the stiffness of the bone cement composition after curing/hardening. While not wishing to be bound by any particular theory, it is believed that lower stiffness is beneficial because it better simulates the actual properties of human bones. The presence of PEG in the aforementioned weight range does not adversely affect the compressive strength and bending strength of the preparation. Thus, the stiffness can be more readily/easily controlled by the presence of PEG, without compromising the compressive and bending strengths of the preparation relative to the prior art preparations. The compressive and bending strengths may be adversely affected when the amount of diluent exceeds 30 wt. %, based on the total weight of the composition. Furthermore, the presence of diluent rapidly destabilizes the radical donor (thus, resulting in a faster hardening of the preparation) and reduces the amount of polymerization accelerator (e.g., DMPT) necessary. If the compression strength of the hardened preparation can be lowered from 30 mega-Pascals (mPa), then the amount of diluent (e.g., PEG) can be increased with a concomitant decrease in the amount of reactive monomer.

The second component generally includes about 1 wt. % to about 90 wt. % of the diluent, based on the total weight of the second component. Preferably, the second component includes about 5 wt. % to about 60 wt. % of the diluent, and even more preferably about 10 wt. % to about 40 wt. % of the diluent, based on the total weight of the second component.

In one embodiment, the second component can also include a radical scavenger. The radical scavenger is present in the second component to retard or arrest the ability of the reactive monomer to self polymerize (self-polymerization is undesirable). The reactive monomer is often sold with sufficient radical scavenger. Preferably, the radical scavenger is selected from the group consisting of hydroquinone, hydroquinone monomethylether, vitamin E, and mixtures thereof.

The amount of the radical scavenger present in the second component generally will depend upon the amount of reactive monomer present. To the extent that additional amounts of radical scavenger are needed/desired, it may be added such that the second component includes about 5 parts per million (ppm) to about 500 ppm of the radical scavenger. Preferably, the radical scavenger is present in the second component in an amount of about 30 ppm to about 400 ppm, and even more preferably about 50 ppm to about 200 ppm.

Optional ingredients present in the second component can include one or more selected from the group consisting of a dye, an admixture of proteins, a chemotherapeutic, a drug, an antibiotic, and mixtures thereof. The admixture of proteins can be an admixture of heat sensitive/unsensitive proteins, which can include mitogenic growth factors, morphogenic growth factors, and mixtures thereof. An example of a suitable drug that can be part of the second component is bisphosphonate. Although the second component can include an antibiotic, preferably the antibiotics when present in the composition are present in the first component.

The bone cement composition is generally prepared by a method that generally includes mixing the first and second components under conditions suitable to form the reaction product. The reaction product preferably is curable under standard pressure (i.e., one bar) and at temperatures ranging from standard temperature (i.e., 25° C.) to about 50° C. The weight ratio of first (dry or powder) component to the second (wet or liquid) component is about 2.2:1 to about 3.3:1, preferably 2.5:1. For example, if the preparation includes ten grams of the first component, then it should include about four grams of the second component.

When the first and second components are combined, a polymerization reaction is initiated by the polymerization accelerator present in the second component and the radical donor present in the first component. In practice, the radical donor will decompose when it encounters the polymerization accelerator evolving a free radical that will attack the double bonds present in the monomer causing the monomer to polymerize and ultimately harden. This reaction in the context of the composition will yield a cured composition In preferred embodiments, the components of the composition are capable of being readily injectable through a syringe-like device or other delivery mechanism to a surgical site, where they react to form the composition and cure to a hardened state. The composition is persistent at the surgical site, preferably adhering to the tissue and/or bone at the site. Furthermore, the composition is stable in that it generally undergoes no significant changes in situ. When set/cured, the composition is also tough and elastic in that it is capable of bearing loads without experiencing undue or permanent deformation. Still further, the composition is believed to be well-tolerated by the body in that it produces, at most, tolerable levels of immune and inflammatory responses. It is to be appreciated, however, that preferred embodiments of the composition, while satisfying at least some of these advantages, may not satisfy all of these advantages in every instance.

In one embodiment, the composition preferably is sold/distributed to users in a kit where the first and second components are maintained apart (e.g., separately packaged or contained) until they are ready for use in forming the composition. The user may receive a mixer apparatus containing the components in separate compartments thereof. See generally, U.S. Pat. No. 6,241,734 and U.S. patent application publication Nos. 2004/0122359 A1 and 2002/0191487 A1, the disclosures of which are incorporated herein by reference. These publications generally describe suitable apparatus for mixing and delivering the composition's components and mixtures thereof to form the composition. The components likely will be mixed by the user immediately prior to the surgical procedure with a suitable mixing apparatus. Once the composition is formed, it should be transferred to an apparatus suitable to deliver the composition (or mixture of components) to the surgical site before the composition (or mixture) sets/cures.

The composition may be applied using a variety of mechanisms such as, for example, those described in U.S. Pat. Nos. 5,972,015 and 6,066,154, the disclosures of which are incorporated herein by reference. These patents generally describe a procedure referred to as "Kyphoplasty," which uses one or two balloons, similar to angioplasty balloons, to reduce the vertebrae bone fracture and restore vertebral height prior to injecting a bone cement composition. For example, two balloons are introduced into the vertebra via bilateral transpedicular cannulae. The balloons are inflated to reduce the fracture, then deflated and removed, leaving a relatively empty cavity into which a bone cement composition is injected. The inflation of the balloons and subsequent injection of the composition helps restore vertebral height.

EXAMPLE

The following example is provided to illustrate an embodiment of the disclosed composition, how it is made, and the results of tests performed on the composition, but is not intended to limit the scope of the disclosure.

Hydroxyapatite was obtained from Merck KGaA (Germany) and was spray-dried by Pharmarone (Germany) and then sintered to provide a sintered, spray-dried hydroxyapatite having a particle size of about 20 μm to about 35 μm. The surface area of the spray-dried and sintered hydroxyapatite was 0.8 $m^2/g$, as determined by BET analysis. A first component (i.e., a dry or powder component) was prepared by combining (a) 7 grams of BPO obtained from Sigma Chemical Company, (b) 120 grams of Plexidon MW 422, which is a prepolymerized vinyl polymer, from Fa. Röhm GmbH (Darmstadt, Germany), (c) 156 grams of sintered, spray-dried hydroxyapatite, and (d) 31.2 grams of barium sulfate. These ingredients are mixed together in a ball mill rotating at a speed of 200 rotations per minute with 405 grams of Steatit balls of 20 mm diameter for 50 minutes. A second component (i.e., the wet or liquid component) was prepared and included (a) 64.6 grams MMA, (b) 5 grams butanediol-dimethacrylate, (c) 30 grams PEG (molecular weight of 400 D), and (d) 0.4 grams DMPT. Ten grams of the first component and 3.5 grams of the second components were mixed together at standard temperature and pressure and were set to provide a hardened material. The handling characteristics were measured at 19.5° C. The dough-time syringe was six minutes 20 seconds, the dough-time bone filler device was seven minutes 20 seconds, and the end dough-time was fifteen minutes.

The material then underwent strength tests. Specifically, the material was subjected to test performed in accordance with ISO 5833 to provide data regarding compressive and bonding strengths. The material had a compressive strength of 30.25 Newtons per square millimeter ($N/mm^2$) measured after two hours, and 30.78 $N/mm^2$ measured after 24 hours. The material had a three-point bending strength of 25.6 MPa after 24 hours and dry incubation, and 37.2 MPa after three days immersion in saline at 37° C. The material had a Young's modulus (elastic modulus) of 1181 MPa after 24 hours dry incubation, and 1532 MPa after three days immersion in saline at 37° C.

The foregoing description is given for clearness of understanding only, and no unnecessary limitations should be understood therefrom, as modifications may be apparent to those having ordinary skill in the art.

What is claimed is:

1. A kit for bone cement comprising:
   a first component comprising a spray-dried hydroxyapatite, a radical donor and poly(methyl methacrylate) (PMMA), wherein the spray-dried hydroxyapatite is present at about 30 wt. % to about 99.5 wt. %, based on the total weight of the first component and has a particle size of about 20 micrometers to about 35 micrometers; and
   a second component comprising a radical scavenger, a diluent, a polymerization accelerator, and a reactive monomer of methyl methacrylate (MMA),
   wherein the reactive monomer of MMA comprises about 40 wt. % to about 95 wt. % of the second component,
   wherein the first component and second component in the bone cement are present in a weight ratio of about 2.2:1 to about 3.3:1.

2. The kit of claim 1, further comprising an apparatus suitable to mix the first and second components.

3. The kit of claim 1, further comprising an apparatus suitable to deliver a mixture of the first and second components to a surgical site.

4. The kit of claim 1, wherein the first component further comprises an optional ingredient selected from the group consisting of an antibiotic, a cytostatic agent, an analgesic agent, a disinfectant, a preservative, a growth factor, a proliferative factor, a protein, a peptide, a biopolymer, an imageable marker, a dye, and mixtures thereof.

5. The kit of claim 4, wherein the imageable marker is selected from the group consisting of barium sulfate ($BaSO_4$, zirconium dioxide, $CHI_3$, $Na_2FPO_3$, and $CaF_2$, and mixtures thereof.

6. The kit of claim 1, wherein the second component further comprises an optional ingredient selected from the group consisting of a dye, an admixture of proteins, a chemotherapeutic, a drug, an antibiotic, and mixtures thereof.

7. The kit of claim 6, wherein the admixture of proteins is selected from the group consisting of mitogenic growth factors, morphogenic growth factors, and mixtures thereof.

8. The kit of claim 6, wherein the drug is a bisphosphonate.

9. The kit of claim 1, wherein the radical donor is selected from the group consisting of benzoyl peroxide (BPO), azo-bis-isobutyrylnitrile (AIBN), and mixtures thereof.

10. The kit of claim 1, wherein the radical scavenger is selected from the group consisting of hydroquinone, hydroquinone monomethylether, vitamin E, and mixtures thereof.

11. The kit of claim 1, wherein the diluent is selected from the group consisting of polyethylene glycol (PEG), an ester of mellitic acid, and mixtures thereof.

12. The kit of claim 1, wherein the first component comprises about 0.5 wt. % to about 5 wt. % of the radical donor, based on the total weight of the spray-dried hydroxyapatite and the PMMA.

13. The kit of claim 1, wherein the first component comprises an imageable marker that comprises up to 30 wt. % of the first component, based on the total weight of the first component.

14. The kit of claim 1, wherein the first component comprises an imageable marker that comprises up to 10 wt. % of the first component, based on the total weight of the first component.

15. The kit of claim 1, wherein the diluent is polyethylene glycol (PEG) having a molecular weight of about 800 D.

16. The kit of claim 1, wherein the first component comprises about 30 wt. % of PMMA based on the total weight of the first component.

17. The kit of claim 1, wherein the radical scavenger comprises about 30 parts per million to about 400 parts per million of the second component.

18. The kit of claim 1, wherein the spray-dried hydroxyapatite has a surface area of 0.8 m²/g.

19. A kit for bone cement comprising:
- a first component comprising a spray-dried hydroxyapatite, benzoyl peroxide (BPO), barium sulfate (BaSO₄) and poly(methyl methacrylate) (PMMA), wherein the spray-dried hydroxyapatite is present at about 30 wt. % to about 99.5 wt. %, based on the total weight of the first component and has a particle size of about 20 micrometers to about 35 micrometers; and
- a second component comprising hydroquinone monomethylether, a diluent, dimethylparatoluidine (DMPT), and a reactive monomer of methyl methacrylate (MMA),
- wherein the reactive monomer of MMA comprises about 60 wt. % to about 90 wt. % of the second component,
- wherein the first component and second component in the bone cement are present in a weight ratio of about 2.2:1 to about 3.3:1.

20. A kit for bone cement comprising:
- a first component comprising a spray-dried hydroxyapatite, a radical donor and poly(methyl methacrylate) (PMMA), wherein the spray-dried hydroxyapatite is present at about 30 wt. % to about 99.5 wt. % based on the total weight of the first component and has a particle size of about 20 micrometers to about 35 micrometers; and
- a second component comprising a radical scavenger, a diluent, a polymerization accelerator, and a reactive monomer of methyl methacrylate (MMA),
- wherein the first component and second component in the bone cement are present in a weight ratio of about 2.2:1 to about 3.3:1.

* * * * *